United States Patent [19]
Bok et al.

[11] Patent Number: 5,877,208
[45] Date of Patent: Mar. 2, 1999

[54] NARINGIN AND NARINGENIN AS 3-HYDROXY-3-METHYLGLUTARYL COA (HMG-COA) REDUCTASE INHIBITOR

[75] Inventors: Song-Hae Bok; Kwang-Hee Son; Tae-Sook Jeong; Byoung-Mog Kwon; Young-Kook Kim; Doil Choi; Sung-Uk Kim; Ki-Hwan Bae, all of Daejeon; Yong-Bok Park; Myung-Sook Choi, both of Daegu; Ingyu Hwang, Daejeon; Surk-Sik Moon, Gongju-shi; Yong-Kook Kwon, Daejeon; Jung-Ah Ahn, Daejeon; Eun-Sook Lee, Daejeon, all of Rep. of Korea

[73] Assignee: Korea Institute of Science and Technology, Seoul, Rep. of Korea

[21] Appl. No.: 949,791

[22] Filed: Oct. 14, 1997

[30]    Foreign Application Priority Data

Oct. 14, 1996 [KR] Rep. of Korea ................. 1996 45735

[51] Int. Cl.⁶ ............................ A61K 31/35; A61K 31/70
[52] U.S. Cl. .............................................. 514/456; 514/27
[58] Field of Search ........................ 514/27, 456

[56]         References Cited

FOREIGN PATENT DOCUMENTS 1179019   1/1970   United Kingdom .

OTHER PUBLICATIONS

Pharmacol. Ther. 67(3):433–447, 1995, "New Targets For Lipid Lowering And Atherosclerosis Prevention", C.R. Sirtori.

"Molecular Biology Of The Cell", Third Edition, Garland Publishing, Inc. Bruce Alberts et al., p. 83 (1994).

"Principles of Biochemistry", 2nd Edition, Worth Publishers, AL Lehninger, 670–673 (1993).

McGilvery, R.W., Biochemistry, pub. W.B.Saunders, p. 593, 1970.

Choi, J. Nat. Products, 54(1), pp. 218–224, Jan., Feb. 1991.

Primary Examiner—Phyllis G. Spivack
Attorney, Agent, or Firm—Anderson, Kill & Olick, P.C.

[57]           ABSTRACT

A method for inhibiting the activity of 3-hydroxy-3-methylglutaryl CoA(HMG—CoA) reductase in mammals is disclosed comprising administering naringin or naringenin thereto.

6 Claims, No Drawings

NARINGIN AND NARINGENIN AS 3-HYDROXY-3-METHYLGLUTARYL COA (HMG-COA) REDUCTASE INHIBITOR

FIELD OF THE INVENTION

The present invention relates to a method for inhibiting the activity of 3-hydroxy-3-methylglutaryl CoA(HMG—CoA) reductase in a mammal which comprises administering naringin or naringenin thereto.

BACKGROUND OF THE INVENTION

In recent years, coronary cardio-circulary diseases, e.g., atherosclerosis and hypercholesterolemia, have increasingly become a major cause of deaths. It has been reported that an elevated plasma cholesterol level causes the deposition of fat, macrophages and foam cells on the wall of blood vessels, such deposit leading to plaque formation and then to atherosclerosis (Ross, R., Nature, 362, 801–809(1993)). One of the methods for decreasing the plasma cholesterol level is alimentotherapy to reduce the ingestion of cholesterol and lipids. Another method is to lower the rate of cholesterol biosynthesis which takes place in the liver. It has been reported that hypercholesterolemia can be treated effectively by reducing the rate of cholesterol biosynthesis through the inhibition of HMG—CoA reductase which mediates the synthesis of mevalonic acid, an intermediate in the biosynthesis of sterols or isoprenoids (Cardiovascular Pharmacology, William W. Parmley and Kanu Chatterjee Ed., Wolfe Publishing, pages 8.6–8.7, 1994).

Therefore, numerous efforts have been made to develop medicines to inhibit HMG—CoA reductase; and, as a result, several compounds derived from Penicillium sp. and Aspergillus sp. have been commercialized. Specifically, Lovastatin® and Simvastatin® developed by Merck Co., U.S.A., and Pravastatin® developed by Sankyo Co., Japan, have been commercialized (C. D. R. Dunn, Stroke: Trends, Treatment and Markets, SCRIPT Report, PJB Publications Ltd., 1995). However, these medicines are very expensive and a long-term administration thereof is known to induce an adverse side effect of increasing creatine kinase in the liver. Accordingly, there has continued to exist a need to develop an inexpensive and non-toxic inhibitor of HMG—CoA reductase.

Naringin and the aglycon of naringin, naringenin, are flavonoids found in lemons, grapefruits, tangerines and oranges (Citrus sinensis) and they have the following structures (Horowitz, Gentili, Tetrahedron, 19, 773(1963)):

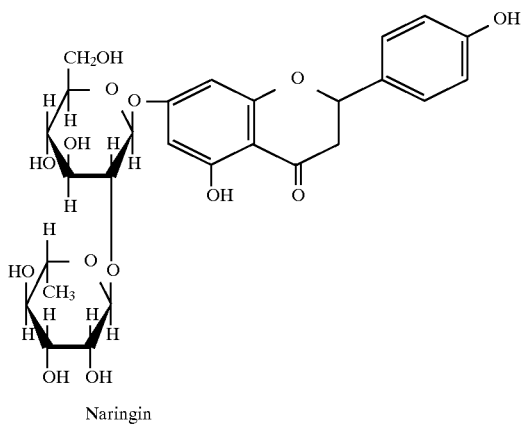

Naringin

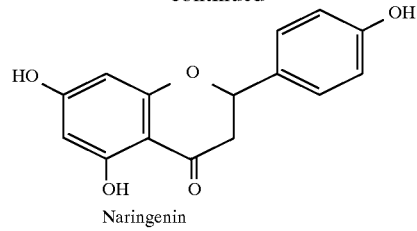

Naringenin

Naringin has been used as a bitter tasting agent, sweetner or chewing gum base. However, there has been no report on the HMG—CoA reductase inhibitory activity of naringin or naringenin.

SUMMARY OF THE INVENTION

Accordingly, it is a primary object of the present invention to provide a method for inhibiting the HMG—CoA reductase activity in mammals.

In accordance with one aspect of the present invention, there is provided a method for inhibiting the HMG—CoA reductase activity in mammals which comprises administering naringin or naringenin thereto.

DETAILED DESCRIPTION OF THE INVENTION

The method of the present invention for inhibiting the activity of HMG—CoA in mammal comprises administering naringin or naringenin thereto.

Naringin and naringenin may be extracted from the peel of citrus or synthesized according to the process described by Rosenmund, Rosenmund, Ber., 61, 2608(1958) and Zemplen, Bognar, Ber., 75, 648(1942). Further, naringenin can be prepared by the hydrolysis of naringin.

Naringin or naringenin exerts an inhibitory effect on the HMG—CoA reductase at a dose of 0.05 mg/kg/day or more, the inhibitory effect increasing with the dose thereof.

Moreover, in spite of their potent efficacies, naringin and naringenin show little toxicity or mitogenicity in tests using mice. More specifically, naringin exhibits no toxicity when it is orally administered to a mouse at a dosage of 1,000 mg/kg, which corresponds to oral administration dose of 50 to 100 g/kg body weight of naringin for a person weighing 50 kg. Further, naringin and naringenin exert no adverse effects on the liver function.

The present invention also provides a pharmaceutical composition for inhibiting the HMG—CoA reductase activity, which comprises naringin or naringenin as an active ingredient, in combination with pharmaceutically acceptable excipients, carriers or diluents.

A pharmaceutical formulation may be prepared by using the composition in accordance with any of the conventional procedures. In preparing the formulation, naringin or naringenin is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. In case of human, a typical daily dose of naringin or naringenin may range from about 0.05 to 300 mg/kg body weight, preferably 0.5 to 30 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, naringin and naringenin can be incorporated in foods or beverages for the purpose of inhibiting the HMG—CoA reductase activity.

As described above, naringin or naringenin can be used as an effective, non-toxic pharmaceutical agent for inhibiting HMG—CoA reductase activity.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Administration of Naringin and Naringenin to an Animal 30 four-week-old Sprague-Dawley rats (Taihan laboratory animal center, Korea) each weighing about 90 to 110 g were evenly divided into three dietary groups by a randomized block design. The rats of the three groups were fed with three different high-cholesterol diets, i.e., AIN-7.6 laboratory animal diet (ICN Biochemicals, Cleveland, Ohio, U.S.A.) containing 1% cholesterol (Control group), 1% cholesterol plus 0.1% naringin (Naringin group), and 1% cholesterol plus 0.1% naringenin (Naringenin group), respectively. The compositions of diets fed to the three groups are shown in Table I.

TABLE I

| Dietary group Component | Control group | Naringin group | Naringenin group |
| --- | --- | --- | --- |
| Casein | 20 | 20 | 20 |
| D,L-methionine | 0.3 | 0.3 | 0.3 |
| Corn starch | 15 | 15 | 15 |
| Sucrose | 49 | 48.9 | 48.9 |

TABLE I-continued

| Dietary group Component | Control group | Naringin group | Naringenin group |
| --- | --- | --- | --- |
| Cellulose powder[*1] | 5 | 5 | 5 |
| Mineral mixture[*1] | 3.5 | 3.5 | 3.5 |
| Vitamin mixture[*1] | 1 | 1 | 1 |
| Choline citrate | 0.2 | 0.2 | 0.2 |
| Corn oil | 5 | 5 | 5 |
| Cholesterol | 1 | 1 | 1 |
| Naringin[*2] | | 0.1 | |
| Naringenin[*2] | | | 0.1 |
| Total | 100 | 100 | 100 |

[*1]Purchased from TEKLAD Premier Co. (Madison, WI, U.S.A.).
[*2]Purchased from Sigma Chemical Company (St. Louis, Mo., U.S.A.)

The rats were allowed to feed freely on the specified diet together with water for six weeks, the ingestion amount was recorded daily and the rats were weighed every 7 days, and then the record was analyzed. All rats showed a normal growth rate and there was observed no significant difference among the three groups in terms of the feed ingestion amount and the weight gain.

EXAMPLE 2

Determination of Total Cholesterol, HDL-Cholesterol and Neutral Lipid Content in Plasma The effect of administering naringin and naringenin to rats on the plasma cholesterol and neutral lipid content was determined as follows.

Blood samples were taken from the rats of the three dietary groups and plasma HDL fractions were separated therefrom by using HDL-cholesterol reagent (Sigma Chemical Co., Cat. No. 352-3) containing dextran-sulfate. Total cholesterol and HDL-cholesterol levels were determined by using Sigma Diagnostic Kit Cat. No. 352-100 (Sigma Chemical Co., U.S.A.) (Allain et al., *Clin. Chem.*, 20, 470–475(1974)). Neutral lipids level was determined by using Sigma Diagnostic Kit Cat. No. 339-50 (Bucolo, G. and David, H., *Clin. Chem.*, 19, 476–482(1973)). The result is shown in Table II, wherein the total plasma cholesterol level decreased by 32% in the naringin fed rat group and by 18% in the naringenin fed rat group, as compared with that of the control group.

TABLE II

| Group Lipids Conc. | Control group | Naringin group | Naringenin group |
| --- | --- | --- | --- |
| Total-C (mg/dl) | 147.8 ± 34.8 | 100.8 ± 16.1 | 120.9 ± 25.9 |
| HDL-C (mg/dl) | 22.2 | 24.0 | 23.4 |
| HDL-C (%) | 15.7 ± 5.3 | 23.9 ± 7.6 | 20.8 ± 9.1 |
| Total-C TG (mg/dl) | 99.2 ± 18.9 | 86.7 ± 14.6 | 103.4 ± 18.2 |

* Total-C: Total-cholesterol
* HDL-C: HDL-cholesterol
* TG: Triglyceride

EXAMPLE 3

Activity of Naringin and Naringenin in HMG—CoA Reductase Inhibition (Step 1) Preparation of Microsomes To determine the effect of naringin and naringenin feeding to rats on the activity of HMG—CoA reductase, a regulatory enzyme of the cholesterol synthesis in the liver, microsomes were separated from the liver tissue to be used as an enzyme source.

First, the rats of the three groups were sacrificed by decapitation and the livers were excised and immediately placed in an ice-cold homogenization medium (50 mM $KH_2PO_4$ (pH 7.0), 0.2M sucrose, 2 mM dithiothreitol (DTT)). The livers were homogenized in the homogenization medium (2 ml medium/g of the liver) with a Waring blendor for 15 sec. (three strokes with a motor-driven Teflon pestle in a Potter-Elvehjem type glass homogenizer). The homogenate was centrifuged at 15,000×g for 10 min. and the supernatant thus obtained was centrifuged at 100,000×g for 75 min. to obtain microsomal pellets, which were then resuspended in the homogenization medium containing 50 mM EDTA and centrifuged at 100,000×g for 60 min. The supernatant containing the microsome was used as an enzyme source.

(Step 2) HMG—CoA Reductase Assay

The activity of HMG—CoA reductase was determined by employing [$^{14}$C]HMG—CoA, in accordance with the method of Shapiro et al. (*Biochemica et Biophysica Acta*, 370, 369–377(1974)) as follows.

The enzyme in the supernatant containing the microsome obtained in (Step 1) was activated at 37° C. for 30 min. Added to a reaction tube were 20 µl of HMG—CoA reductase assay buffer (0.25M $KH_2PO_4$(pH 7.0), 8.75 mM EDTA, 25 mM DTT, 0.45M KCl and 0.25 mg/ml BSA), 5 µl of 50 mM NADPH, 5 µl of [$^{14}$C]HMG—CoA (0.05 µCi/tube, final conc. 120 µM), and 10 µl of activated microsomal enzyme (0.03–0.04 mg), and the mixture was incubated at 37° C. for 30 min. The reaction was terminated by adding 10 µl of 6M HCl to the mixture, and the mixture was incubated at 37° C. for 15 min. to allow complete lactonization of the product (mevalonate). The precipitate was removed by centrifugation at 10,000×g for 1 min. and the supernatant was applied to a Silica gel 60G TLC plate (Altech, Inc., Newark, U.S.A.) and then developed with benzene:acetone (1:1, v/v). A region having a Rf value ranging from 0.65 to 0.75 was removed by scraping with a disposable cover slips and assayed for radioactivity with 1450 Microbeta liquid scintillation counter (Wallacoy, Finland). Enzyme activities were calculated as picomoles mevalonic acid synthesized per min. per mg protein (pmoles/min/mg protein). The result is shown in Table III.

TABLE III

| Group | Control group | Naringin group | Naringenin group |
|---|---|---|---|
| HMG-CoA reductase activity (pmole/min/mg protein | 147 ±12.5 | 111.1 ±14 | 101.4 ±7.3 |

As can be seen from Table III, the control group rats showed a relatively high HMG—CoA reductase activity, while the HMG—CoA activities observed with the naringin-fed rat group and the naringenin-fed rat group are lower than that of the control group by 25% and 31%, respectively.

EXAMPLE 4

Toxicity of Orally Administered Naringin 7 to 8 week-old, specific pathogen-free ICR female mice (8 heads) each weighing about 25 to 29 g and male mice (8 heads) each weighing about 34 to 38 g were bred under a condition of temperature 22°±1° C., moisture 55±5% and photoperiod 12L/12D. Fodder (Cheiljedang Co., mouse and rat fodder) and water were sterilized and fed to the mice.

Naringin was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of naringin. Further, on the 10th day, the mice were sacrificed and the internal organs were visually examined.

All the mice were alive at day 10 and naringin showed no toxicity at a dose of 1,000 mg/kg. The autopsy revealed that the mice did not develop any pathological abnormality, and no weight loss was observed during the 10 day test period. Accordingly, it was concluded that naringin is not toxic when orally administered to an animal.

The following Formulation Example is for illustration only and not intended to limit the scope of the invention in any way.

FORMULATION EXAMPLE

Hard gelatin capsules were prepared using the following ingredients:

| | Quantity (mg/capsule) |
|---|---|
| Active ingredient(naringin) | 20 |
| Starch, dried | 160 |
| Magnesium stearate | 20 |
| Total | 200 mg |

While the invention has been described with respect to the above specific embodiments, it should be recognized that various modifications and changes may be made to the invention by those skilled in the art which also fall within the scope of the invention as defined by the appended claims.

What is claimed is:

1. A method for inhibiting the activity of 3-hydroxy-3-methylglutaryl CoA(HMG—CoA) reductase in a mammal which comprises administering an effective amount of naringin or naringenin thereto.

2. The method of claim 1, wherein the mammal is human.

3. The method of claim 2, wherein the effective amount of naringin ranges from 0.05 to 300 mg/kg body weight/day.

4. The method of claim 2, wherein the effective amount of naringenin ranges from 0.05 to 300 mg/kg body weight/day.

5. The method of claim 1, wherein said naringin or naringenin is administered in the form of a pharmaceutical composition.

6. The method of claim 1, wherein said naringin or naringenin is administered in the form of an additive or a dietary supplement in food or beverage.

* * * * *

UNITED STATES PATENT AND TRADEMARK OFFICE
CERTIFICATE OF CORRECTION

PATENT NO. : 5,877,208
DATED : March 2, 1999
INVENTOR(S) : Song-Hae Bok, et al

It is certified that error appears in the above-identified patent and that said Letters Patent is hereby corrected as shown below:

On the title page, item [30], should read

Foreign Application Priority Data

Oct. 14, 1996  [KR]  Rep. of Korea    96-45735

Signed and Sealed this

Sixth Day of July, 1999

Attest:

Q. TODD DICKINSON

*Attesting Officer*    *Acting Commissioner of Patents and Trademarks*